(12) United States Patent
Motoyama

(10) Patent No.: US 6,525,315 B1
(45) Date of Patent: Feb. 25, 2003

(54) ULTRAVIOLET LIGHT PERMEABLE FILTER FOR FLAW DETECTION LIGHT, AND METHOD FOR DETECTION OF FLAWS

(75) Inventor: Masami Motoyama, Chiba-ken (JP)

(73) Assignee: Marktec Corporation, Tokyo (JP)

( * ) Notice: Subject to any disclaimer, the term of this patent is extended or adjusted under 35 U.S.C. 154(b) by 0 days.

(21) Appl. No.: 09/593,683

(22) Filed: Jun. 14, 2000

(30) Foreign Application Priority Data

Nov. 29, 1999 (JP) .......................................... 11-338041

(51) Int. Cl.[7] .............................................. G01N 21/64
(52) U.S. Cl. ................. 250/302; 250/504 H; 250/461.1
(58) Field of Search ............................... 250/302, 237, 250/301, 504 H, 461.1

(56) References Cited

U.S. PATENT DOCUMENTS 3,774,030 A  * 11/1973  O'Connor et al. .......... 250/302
4,793,669 A  * 12/1988  Perilloux ..................... 350/1.6
5,804,822 A  *  9/1998  Brass et al. .................. 250/302

OTHER PUBLICATIONS

Japanese Patent Office, Utility Model Publication, Registration No. 3027343, Publication Date: May 22, 1996, Application No. 8–920, Application Date: Jan. 29, 1996, With English Abstract.

Japanese Patent Office, Patent Publication, Publication No.: 3–1249, Publication Date: Jan. 10, 1991, Application No. 60–163923, Application Date: Jul. 26, 1985, With English Abstract.

Japanese Patent Office, Patent Publication, Publication No. 48–8722, Publication Date: Mar. 17, 1973, Application No. 44–82744, Application Date: Oct. 17, 1969, With English Abstract.

* cited by examiner

Primary Examiner—John R. Lee
Assistant Examiner—David A Vanore
(74) Attorney, Agent, or Firm—Snider & Associates; Ronald R. Snider

(57) ABSTRACT

An ultraviolet light permeable filter for an ultraviolet detection light is equipped on a filter glass surface with a dielectric multi-film layer which allows a visible radiation of wave length from 694 nm to 780 nm to reflect on the layer. The wave length also does not penetrate through the multi-flim layer. This filter prevents a reddish halation occurrence during an inspection display of a flaw detection light, which is the main cause of overlooking a scratch or flaw pattern.

3 Claims, 8 Drawing Sheets

ULTRAVIOLET LIGHT PERMEABLE FILTER FOR FLAW DETECTION LIGHT, AND METHOD FOR DETECTION OF FLAWS

This present disclosure relates to subject matter contained in Japanese Patent Application No.11-338041 (filed on Nov. 29, 1999) which is expressly incorporated herein by reference in its entirety

BACKGROUND OF THE INVENTION

The present invention relates to an ultraviolet light permeable filter for a flaw detection light and a method for a detection of flaws.

In a prior art, according to JIS (Japan Industrial Standard), in order to perform a fluorescent penetrant liquid detection method test and a fluorescent magnetic powder detection (=magnaflux) method test, an ultraviolet detection light (this is also called a black light among those skilled in the art) is adopted, wherein the light is emitted from a metal halide lamp and an ultraviolet light filter so that the fluorescent penetrant liquid and magnetic powder are excited to emit radiation.

For example, in the method as already disclosed, the ultraviolet flaw detection light comprising the metal halide lamp and the ultraviolet light permeable filter equipped with a minimum wave length of 385±5 nm which can be recognized with normal eyesight is provided. An inspector can lessen his fatigue or avoid his mistakes caused by fatigue during blue-violet radiation using a wave length below 400 nm.

In the field test of the fluorescent penetrant liquid method or the fluorescent magnetic powder method for checking a flaw on an irregular surface in a minor area where a marketed ultraviolet flaw detection light comprising the ultraviolet light permeable filter and the metal halide lamp is used, a serious problem exists. The inspector has difficulty in checking the flaw because he is forced to recognize with his eyes a reddish halation mixed by a red and pale blue radiations which are caused by reflected light from a test display according to the angle between radiated light and the inspector's eyes toward the display. When the flaw exists on the spot of the halation, especially a reddish halation, the inspector might miss checking the relative flaw. As a result, an accurate flaw detection cannot be attained by the inspection on an irregular surface in a minor area for finished work.

SUMMARY OF THE INVENTION

The present inventor has done research and experiments to provide an ultraviolet light permeable filter which prevents the occurrence of halation, especially reddish halation which is the main cause of overlooking a flaw during the inspection. As a result, this inventor has confirmed that visible radiation wave length in the ranges of 380 nm~410 nm and 694 nm~780 nm penetrates through a prior marketed ultraviolet light permeable filter. This prior art uses various kinds of ultraviolet flaw detection lights composed of metal halide lamps. The radiation in the above ranges reflects on the test display to produce a reddish halation. At the same time, the inventor has found that the reddish halation is avoided when the radiation in the range of 694 nm~780 nm does not penetrate the filter.

In order to realize the above purpose, the following procedures are adopted.

This invention provides a device of a dielectric multi-film layer which is formed on the surface of the ultraviolet light permeable filter glass, whereas visible radiation in the range of 694 nm~780 nm reflects on the filter and does not penetrate therethrough.

The invention also provides a device of the filter where the dielectric multi-film layer is composed of plural layers of low refractivity material and of high refractivity material stacked in alternating layers of low refractivity and high refractivity material.

This invention further provides a device of any filter as mentioned so far where the multi-film layer is while a layer of high refractivity material is sandwiched between layers of low refractivity material and the obtained composite is a plurality of layers thick.

Further, the flaw detection light of the present invention is equipped with any of said filters.

DETAILED DESCRIPTIONS OF THE PREFERRED EMBODIMENT

First, the inventor's research and experiments are explained.

Figure 6:
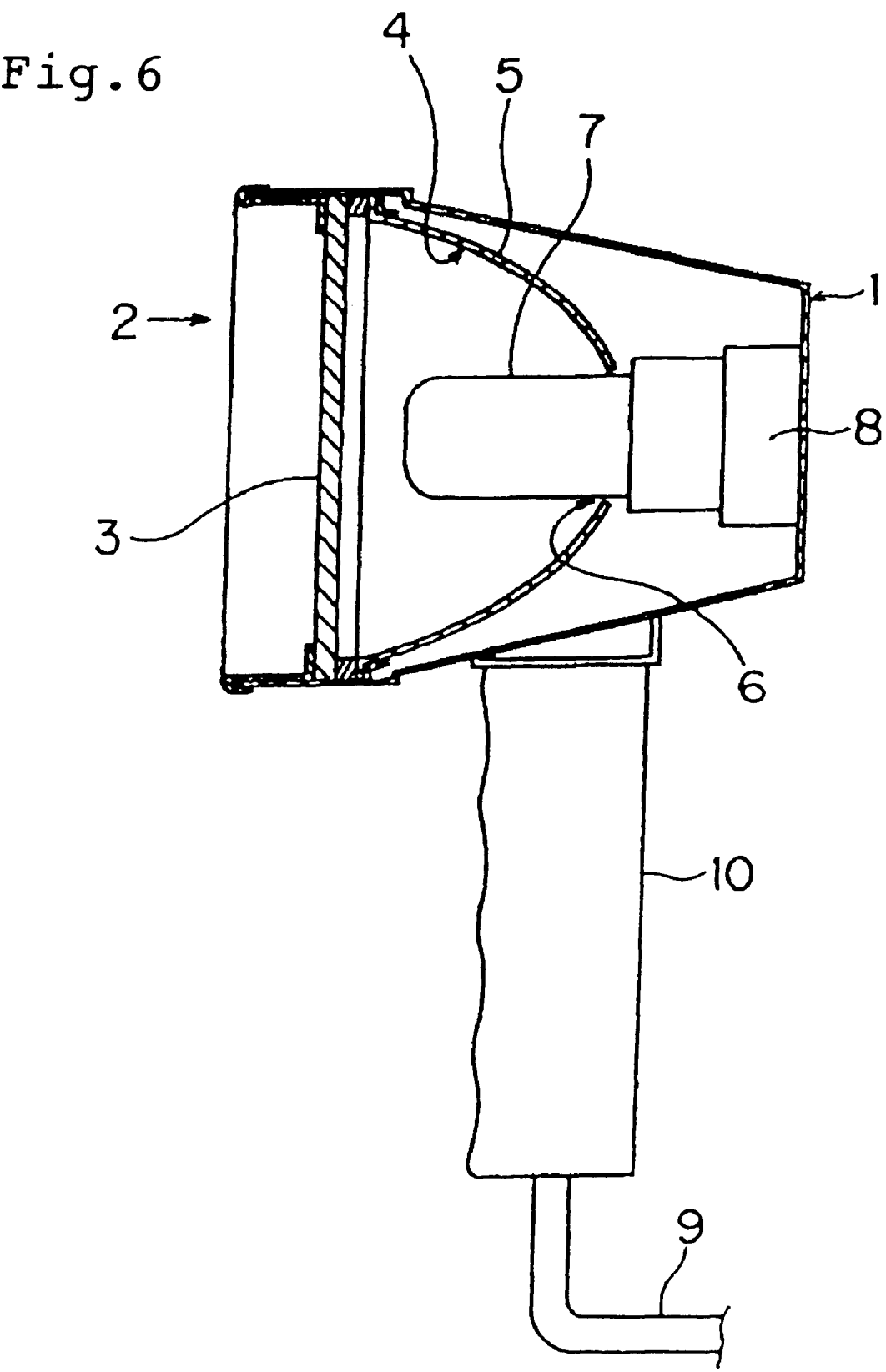
FIG. 6 is a partially schematic side view of a flaw detection light.

With reference to FIG. 6, the numeral 1 is a metal shell having an opening (2) on its side for radiating an ultraviolet light. The numeral 3 is a basic substratum of a filter of the ultraviolet light equipped with the opening (2). At the rear of the filter (3), a concave reflector mirror (5) is arranged with an anodized mirror face (4) which is directed for the filter (3). On the middle portion of the mirror (5), a hole (6) is drilled. The numeral 7 is a metal halide lamp which is inserted into the hole (6) through the back side of the mirror (5), while its basic portion is connected into a socket (8). A power supply binary cord (9) is connected with an inverter (not shown) at the outside of the shell (1). The numeral 10 is a handle portion in which the cord is running through.

Figure 7:
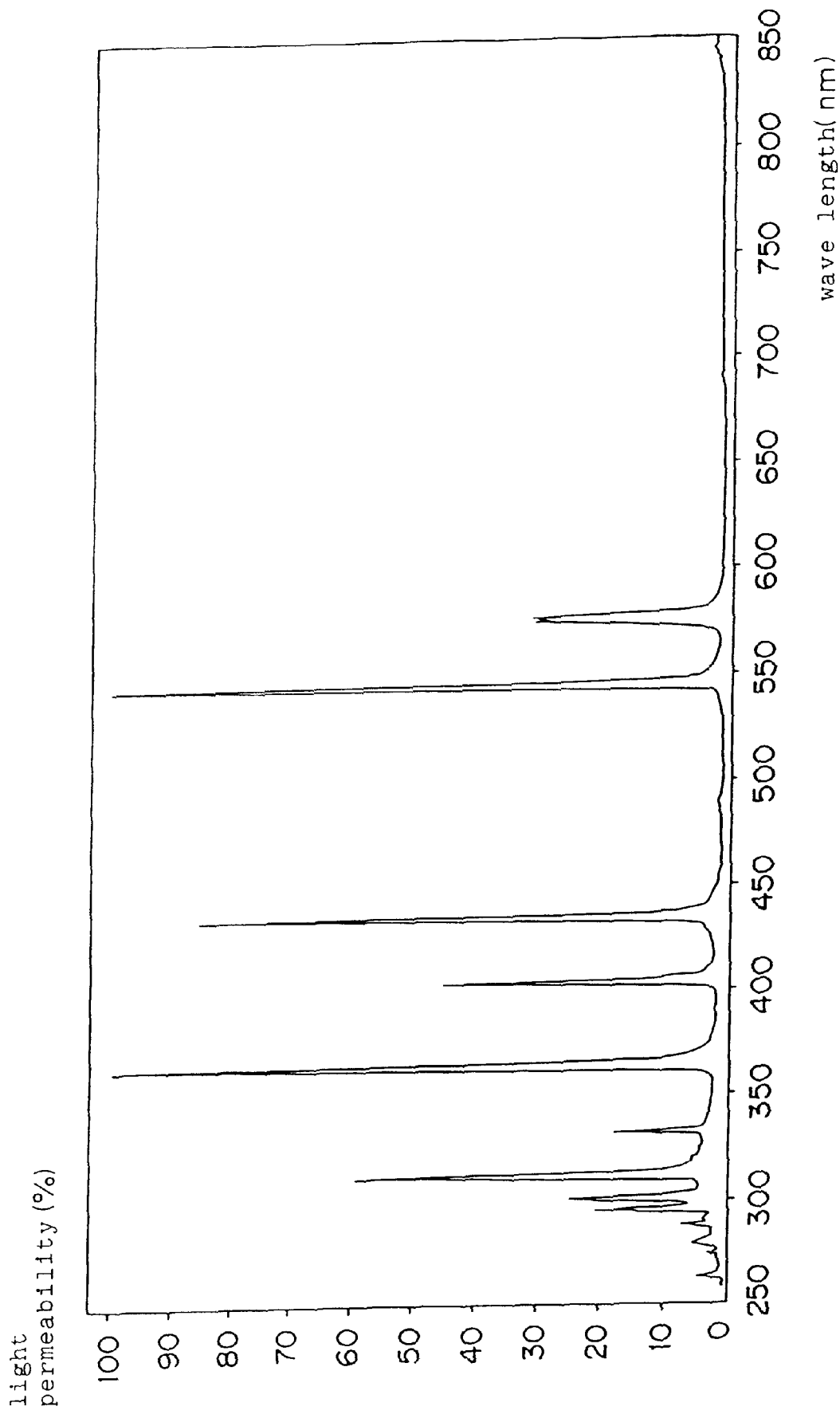
FIG. 7 is a graphical representation of a spectrophotometric curve line obtained by a metal halide lamp in this invention.
Figure 8:
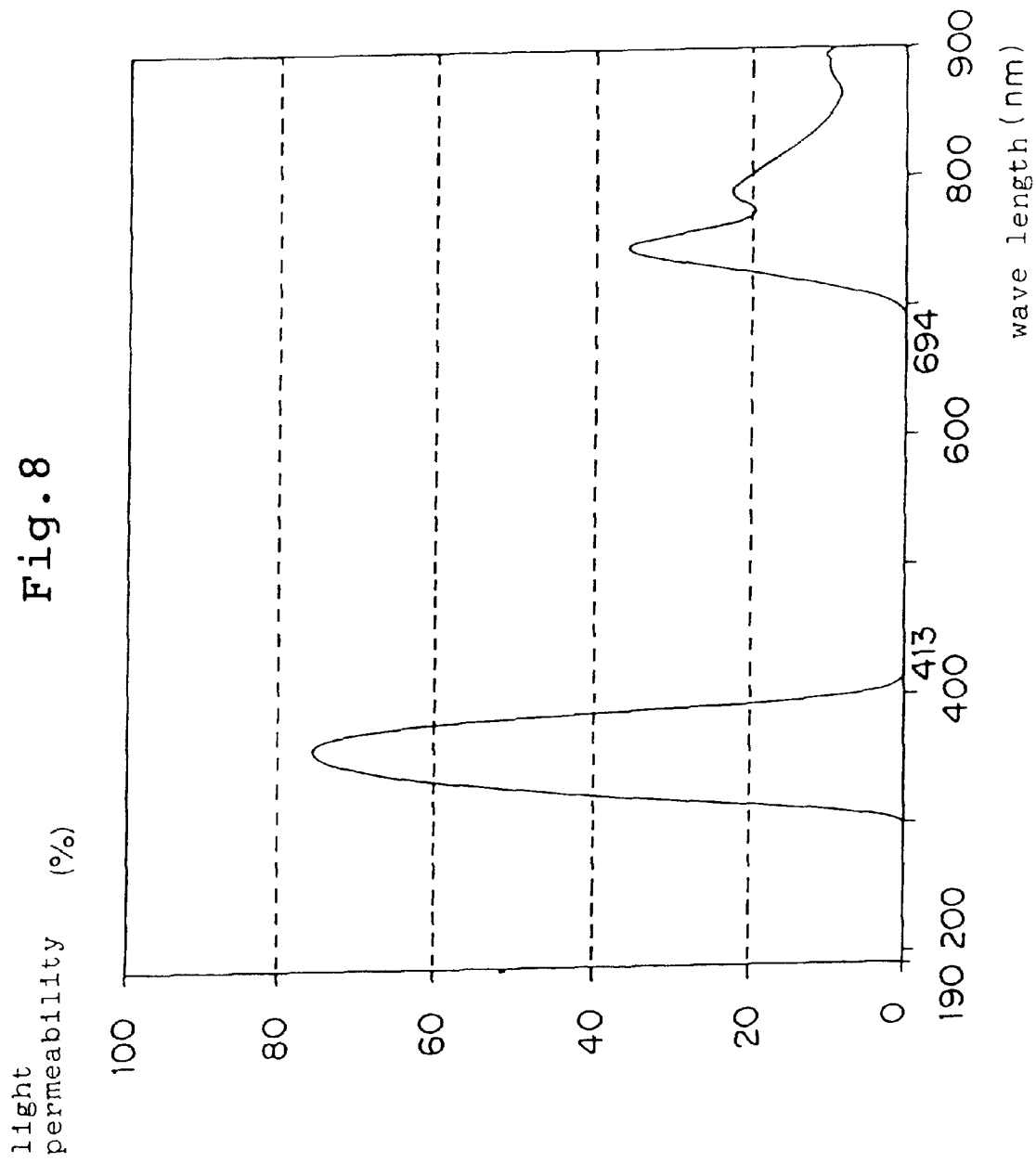
FIG. 8 is a graphical representation of a spectrophotometric curve line obtained by a prior ultraviolet light permeable filter glass.

According to FIG. 7, a graphical representation of a spectrophotometric curve for the metal halide lamp (7) is shown. This lamp is adopted from one marketed in the name of "70W/FDA" supplied by Marktec Corporation. FIG. 8 is a graphical representation of a spectrophotometric curve obtained by a prior ultraviolet light permeable filter glass. This filter is known by the name of "D10FA" marketed by Marktec Corporation wherein no coating is furnished thereupon. As shown in FIG. 8, the filter glass in the prior art, against visible radiation in the wave length range of 380 nm~780 nm, allows the visible radiation in the wave length of 413 nm ~694 nm to be absorbed and the radiation does not penetrate therethrough, while the filter allows the radiation in the wave lengths of 380 nm 413 nm and 694 nm~780 nm to penetrate therethrough.

In order to produce the graphical representation of the curve in this invention, a special spectrophotometer for such presentation developed and supplied by Shimadzu Seisakusho Co., Ltd., model No. U-2200 was used.

TEST

Experimental Material: Steel square column, in the sectional size of 50×50 mm, with 200 mm long.
Scratch: Natural scratch in 20 mm long and 0.12 mm deep on the polished surface.
Fluorescent magnetic powder: Name of "Supermagna LY-50" supplied by Marktec Corporation.
Density of magnetic powder: 0.5 g/l
Dispersing agent: Name of "BC-1" supplied by Marktec Corporation.
Density of dispersing agent: 2 g/l
Electric current value of magnetization: DC-500A Under above conditions, several visual observation tests were performed to watch occurrence of halation on the indicated scratch.

As a first test, a prior art ultraviolet light permeable filter glass was equipped with a flaw detection light and a fluorescent magnetic powder test was performed. As a result, a pale blue halation could not be recognized, but a reddish halation was recognized, which caused overlooking of the indicated scratch thereon.

Figure 9:
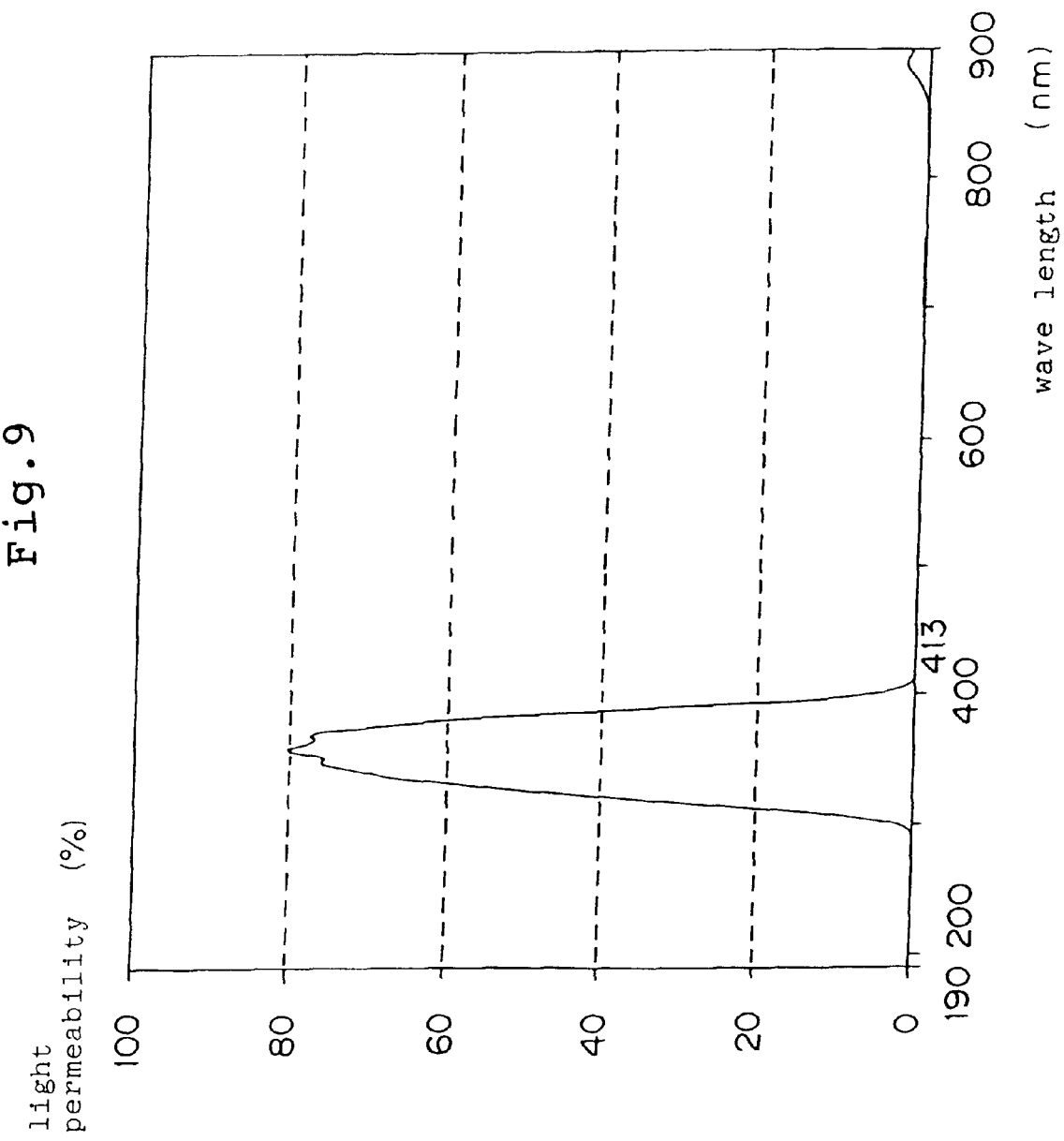
FIG. 9 is a graphical representation of an ultraviolet light permeable filter obtained by this invention.
Figure 10:
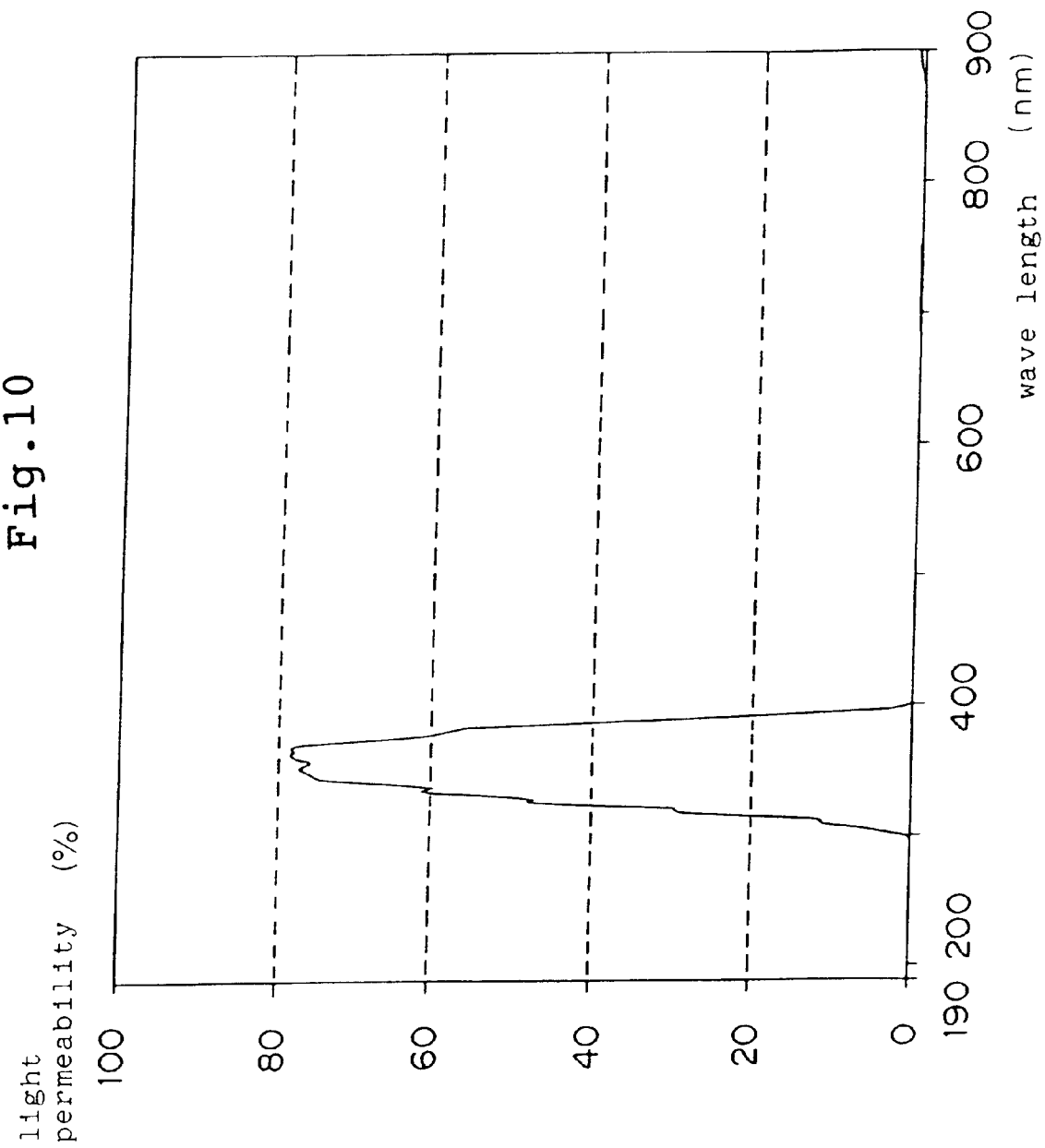
FIG. 10 is a graphical representation of the other ultraviolet light permeable filter obtained by this invention.

In order to improve the result, in stead of the prior art filter, two kinds of the newly invented filters which were equipped with a dielectric multi-film layer obtained by vacuum evaporation method, having graphical representations as shown in the curves of FIG. 9 and FIG. 10, are then tested.

As a second test, the filter which allows the visible radiation over the wave length of 700 nm to reflect and which has the graphical representation of the curve in FIG. 9 was equipped with the flaw detection light and the fluorescent magnetic powder test was performed. As a result, the pale blue halation was recognized while the reddish halation was not recognized, whereas the indicated scratch was clearly observed.

As a third test, the filter which allows the visible radiation in the wave lengths of 400 nm 410 nm and over nearly 700 nm to reflect and which has the graphical representation of the curve in FIG. 10 was equipped with the flaw detection light and the fluorescent magnetic powder test was performed. As a result, the pale blue halation was a little bit recognized while the reddish halation was not recognized, whereas, same as the second test, the indicated scratch was clearly observed.

Through the above three experimentations and obtained results, the present inventor realized that where the radiation in the wave length of nearly 700 nm was recognized as a reddish halation and that the occurrence of this halation was the true source of an inspector's mistake. Therefore, the inventor has developed an ultraviolet light permeable filter which allows the radiation to reflect and not to penetrate in the range of wave length from nearly 700 nm to 780 nm, when this filter is equipped with a flaw detection light, the satisfactory result has been confirmed.

Now, actual embodiments for the present invention are explained according to the attached drawings.

Embodiment 1

Figure 1:
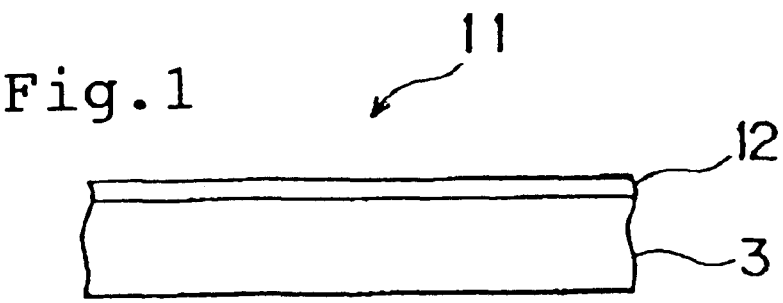
FIG. 1 is a partial diagrammatic view of longitudinal section showing a constitution of an ultraviolet light permeable filter to be equipped with a flaw detection light in an embodiment No.1.
Figure 2:
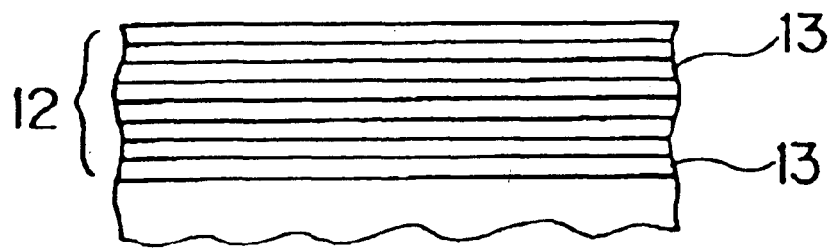
FIG. 2 is a partial longitudinal section view showing enlarged constitution of a plurality layers of the filter as illustrated in FIG. 1.
Figure 3:
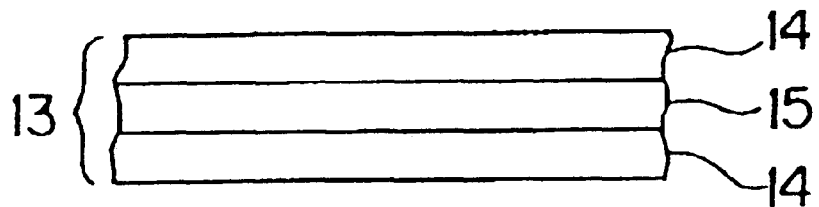
FIG. 3 is a partial longitudinal section view showing enlarged constitution for a single layer (13) which is composed of membranes (14 and 15).

FIG. 1 is a partial diagrammatic view of longitudinal section for an ultraviolet light permeable filter (11) equipped with a flaw detection light, and a constitution of the filter (11) is shown in clarified manners, and the numeral 3 is also the substratum of the filter while the numeral 12 is a multi-film layer having plural layers. FIG. 2 shows a partial longitudinal section view for the multi-film layer (12) enlarged and having plural layers (13). FIG. 3 is also a partial longitudinal section view for an individual layer (13) enlarged, which is again composed of further three membranes (14 and 15). This filter (11) is obtained by forming a dielectric multi-film layer (12), which can reflect a visible radiation with a wave length range of 694 nm~780 nm, on the glass surface of a prior art filter. The layer of the multi-film (12) is composed of 8 layers (13). Each layer (13) is also composed of other membrane layer (14) with low refractivity material and of another membrane layer (15) with high refractivity material, layers (14 and 15) alternately. In this situation, the high refractivity membrane (15) is sandwiched by the low refractivity membranes (14).

The dielectric multi-film layer (12) may be formed by coating thin layers (14,15) in alternate layers through vapour deposition, such as a vacuum evaporation method or an ion plating method as are well known, so that permeable wave length is selectively controlled. The vapour deposition method is inexpensive.

The material for a single layer (13) of the multi-film (12) is selected from a group of high refractivity materials such as $HfO_2$ (Hafnium oxide), $TiO_2$ (Titanium oxide), $ZrO_2$ (Zirconium oxide), Zns (Zinc sulphide) and from a group of low refractivity materials such as $SiO_2$ (Silicon oxide), $MgF_2$ (Magnesium fluoride) and $Na_8AlF_6$ (Cryolite). This individual layer (13) is composed of the low refractivity membranes (14) and the high refractivity membrane (15) in alternate layers. As shown in FIG. 3, the single layer of the multi-film layer is composed in the following manner. First, on the low refractivity membrane (14) of $SiO_2$ material with 146 nm, the high refractivity membrane of $TiO_2$ material with 520 nm is placed, and then on these combined membranes the low refractivity membrane (14) is again placed. Eight layers of this obtained single layer (13) composed of three membranes (14, 15 and 14) are now stacked together, and thus the multi-film layer (12) is completed. Now, the layer (12) is attached on one side surface of the prior filter glass, whereas the visible radiation of wave lengths 694 nm~780 nm reflects on the filter (11) and does not penetrate therethrough.

The dielectric multi-film layer (12) is not necessary composed of 8 layers, and when the number of the layer is increased the reflection degree of the radiation for wave lengths can be properly controlled. The order to alternate the membranes is explained as above, but this order may be changed as: First, the high refractivity membrane (15) is piled on the low refractivity membrane (14).

Embodiment 2

Figure 4:
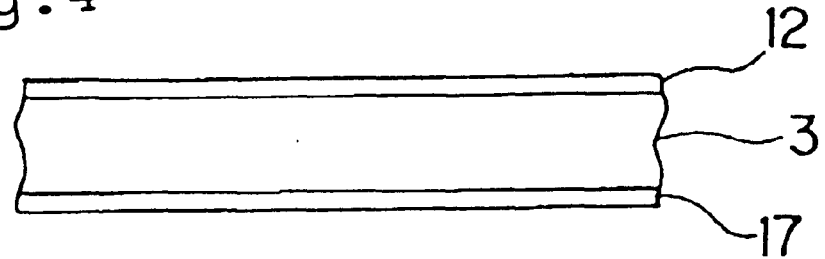
FIG. 4 is a partial longitudinal section view showing a constitution of an ultraviolet light permeable filter for a flaw detection light in accordance with an embodiment No.2.
Figure 5:
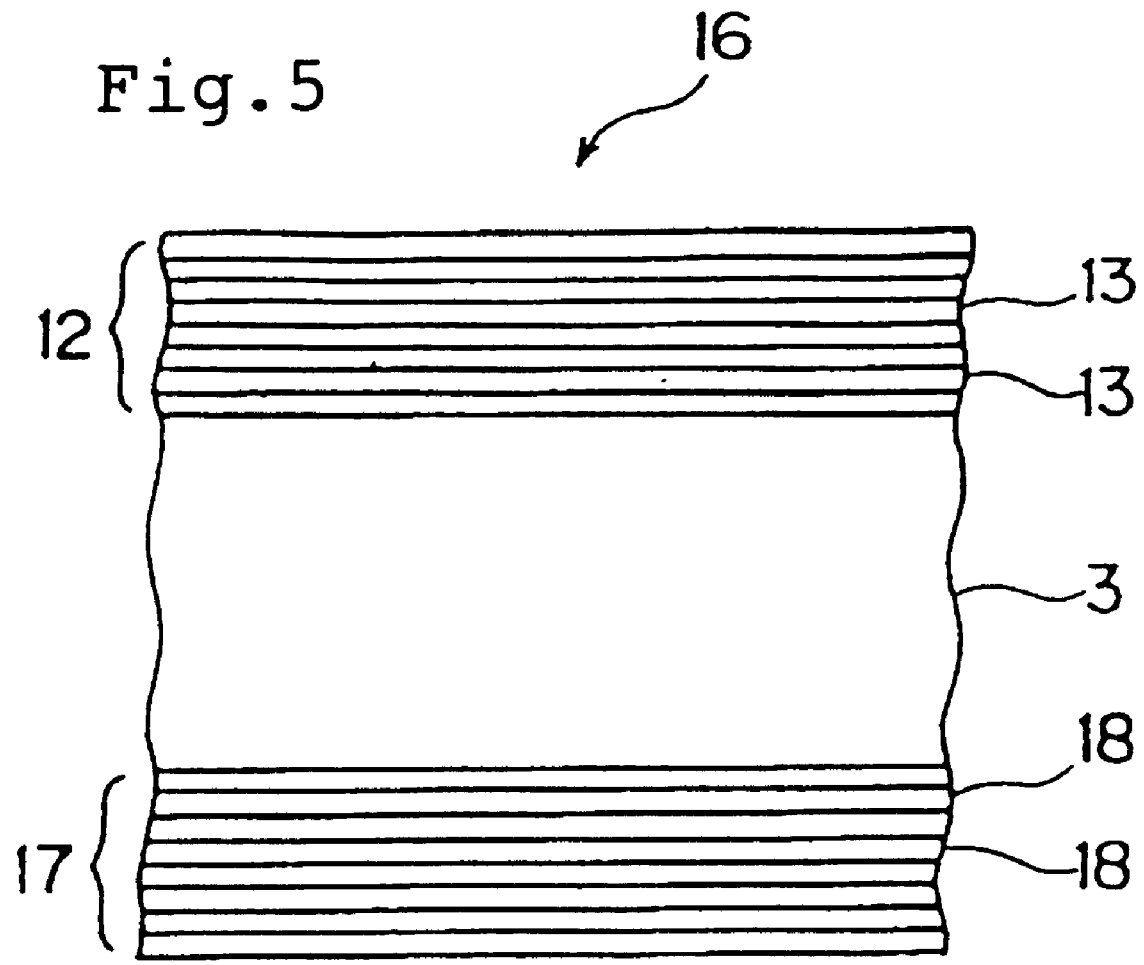
FIG. 5 is a partial longitudinal section view showing an enlarged constitutional condition for a dielectric multi-film layer placed on both surfaces of the filter as illustrated in FIG. 4.

According to FIG. 4, the numeral 16 is an ultraviolet light permeable filter, wherein a multi-film layer (17) is equipped on the other side surface of the previous filter (11) and the layer (17) allows visible radiation at wave length of 400 nm~410 nm to reflect on the layer (17) and this radiation does not penetrate the layer (17). With reference to FIG. 5, the numeral 18 is a single membrane layer which composes of the multi-film layer (17) with 8 layers stacked. This single layer (18) may also be composed of membrane layers (14) with low refractivity material which alternate with membrane layers (15) with high refractivity material as shown in FIG. 3.

As shown in FIG. 5, on the other side surface of the filter (11), the multi-film layer (17) of dielectric quality is attached to substratum (3). Eight single layers (18) are stacked, while the layer (18) comprises : a membrane layer (15) of high refractivity $TiO_2$ material at 325 nm stacked on a membrane layer (14) of low refractivity $SiO_2$ material at 91 nm and further the same low membrane layer (14) is stacked on the same high membrane layer (15), and thus the dielectric multi-film layer (17) is obtained, whereas this dielectric layer (17) allows visible radiation in wave length at 400 nm ~410 nm to reflect on the layer (17) while the radiation does not penetrate therethrough. For further references and clearer understanding, the examples of the present invention are now explained below to teach how to produce the required filters:

EXAMPLE 1

On one surface of an ultraviolet light permeable filter glass (Article Number D10FA supplied by Marktec Corporation without any coating on its glass surface), a multi-film layer (12) is formed. The layer (12) is produced by vacuum thin film evaporation treatment (Article Name and Number-:Automatic successive vacuum thin film forming machine, No. CES-3, supplied by Kabushiki Kaisha Synchron) and this filter before putting the layer (12) had a graphical representation of a spectrophotometric curve shown in FIG. 8. On a low refractivity membrane (14) of SiO2 material with 146 nm, a high refractivity membrane (15) of TiO2 material with 520 nm is placed, and further the same low refractivity membrane (14) is again placed thereon. In other words, the high refractivity membrane (15) is now sandwiched by two low membranes (14) and this three laminated composite becomes a single layer (13) for the multi-film layer (12). Thus, 8 layers of the obtained composite layer (13) are stacked together into the multi-film layer (12). In this method, the ultraviolet light permeable filter (11) is now completed as shown in FIG. 1~FIG. 3.

With this filter (11), the graphical representation of the spectrophotometric curve is checked, and as a result, the relative graph is shown in FIG. 9, wherein the dielectric multi-film layer (12) which allows a visible radiation of wave length 694 nm~780 nm to reflect on the filter (11) and not to penetrate therethrough is now confirmed.

The filter (11) is then equipped with a flaw detection light (Article Name and Number: Super Light D-10, supplied by Marktec Corporation, operated by Metal Halide Lamp 70 W/FDA, also supplied by Marktec Corporation), and tested in the following data:

Experimental Material : Steel square column, in the sectional size of 50×50 mm, with 200 mm long.

Scratch : Natural scratch in 20 mm long and 0.12 mm deep on the polished surface. Fluorescent magnetic powder : Name of "Supermagna LY-50" supplied by Marktec Corporation.

Density of magnetic powder: 0.5g/1

Dispersing agent: Name of "BC-1" supplied by Marktec Corporation.

Density of dispersing agent: 2g/1

Electric current value of magnetization : DC-500A

As a result of the test, pale blue halation is recognized while reddish halation is not recognized, whereas the indicated scratch is clearly observed.

Example 2

Same as the Example 1, on one surface of the ultraviolet light permeable filter glass, the dielectric multi-film layer (12) is formed, while on the other surface of the glass filter, another dielectric multi-film layer (17) is formed. The latter layer is also produced by the vacuum thin film evaporation treatment as mentioned. On a low refractivity membrane of $SiO_2$ material with 91 nm, a high refractivity membrane of $TiO_2$ material with 325 nm is placed, and further said low refractivity membrane is again placed thereon. This three laminated composite becomes a single layer (18) for the multi-film layer (17), and 8 layers of the single layer (18) are stacked together into the multi-film layer (17). Thus, the ultraviolet light permeable filter (16) is obtained as shown in FIG. 4 and FIG. 5.

Figure 11:
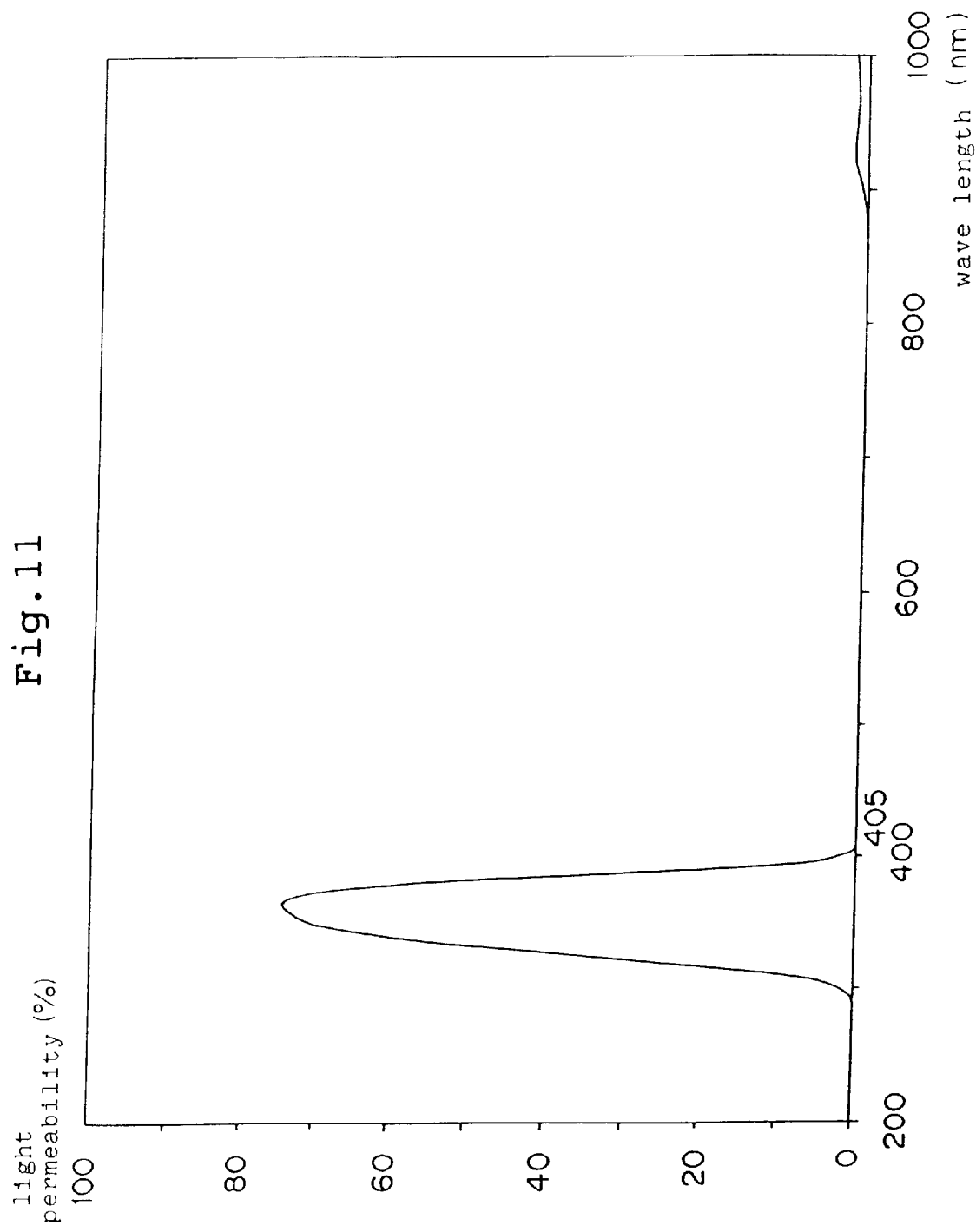
FIG. 11 is a graphical representation of another ultraviolet light permeable filter obtained by this invention.

With this filter (16), the graphical representation of the spectrophotometric curve was checked, and the result showed the graph in FIG. 11, wherein the dielectric multi-film layer (17) which allows a visible radiation of wave length with 405 nm~410 nm to reflect on the filter (16) and not to penetrate therethrough is now confirmed.

Same as Example 1, a test is performed thereof, through which no halation is present with a good result observation of the indicated scratch.

EXAMPLE 3

Same as the Example 1, on one surface of the filter glass, the multi-film layer (12) is formed. The multi-film layer is produced as: On a low refractivity membrane of $MgF_2$ material with 138 nm, a high refractivity membrane of $HfO_2$ material with 440 nm is placed, and further the low refractivity membrane is again placed thereon. This three laminated composite becomes a single layer (13) for the multi-film layer (12) which is composed of 8 piled single layers (13). In this procedures, the filter (11) as shown in FIG. 1~FIG. 3 is obtained.

With this filter (11), when the graphical representation of the spectrophotometric curve is checked, the similar graph shown in FIG. 9 is obtained, whereas the dielectric multi-film layer (12) which allows a visible radiation of wave length with 694 nm~780 nm to reflect on the filter (11) and not to penetrate therethrough is confirmed.

With this obtained filter (11) a test is performed in the same manners as Example 1, whereas blue halation is recognized but reddish halation is not recognized. Because of no existence of the reddish halation the indicated scratch can be clearly observed.

EXAMPLE 4

Same as Example 2, on one surface of the filter glass, the dielectric multi-film layer (12) is formed. This layer (12) is composed of 8 stacks of a single layer (13). The single layer (13) is produced in the following manners: on a low refractivity membrane (14) of $MgF_2$ material with 138 nm, a high refractivity membrane (15) of $HfO_2$ material with 440 nm is placed, and further the low refractivity membrane (14) is again placed thereon. On the other hand, on the other surface of the filter glass, another multi-film layer (17) is formed. The latter layer (17) is also composed of 8 stacks of a single layer (18). The single layer (18) is produced in the manners: On a low refractivity membrane of $MgF_2$ material with 138 nm, a high refractivity membrane of $TiO_2$ material with 325 nm is placed, and further the same low refractivity membrane is again placed thereon. In this procedure, an ultraviolet light permeable filter (16) as shown in FIG. 4 and FIG. 5 is now obtained.

With this filter (16), when the graphical representation of the spectrophotomeric curve is checked, the similar graph shown in FIG. 11 is provided, whereas the dielectric multi-film layer (17) which allows a visible radiation of wave length with 405 nm~410 nm to reflect on the filter (16) and not to penetrate therethrough is confirmed.

With this filter (16) a test is performed in the same manner as the Example 1, whereas no halation is recognized at all, and satisfactory inspection result is attained with proper observation.

As explained so far, the present invention can provide an ultraviolet light permeable filter for a flaw detection light, the filter allowing a visible radiation in the wave length range from 694 nm to 780 nm to reflect on the filter and also allowing the radiation not to penetrate through the filter.

At the same time, when the invented filter as explained in this specification is equipped with an ultraviolet flaw detection light, the flaws and scratches can be promptly and easily found by inspectors, even on plane surfaces and well polished or well finished faces which are very difficult in the prior art.

It is now clearly understood the described invention shall greatly benefit present and relative industrial field for finding flaws or scratches with ease.

It is further understood by those skilled in the art that the foregoing descriptions is a preferred embodiment of the disclosed device and that various changes and modifications may be made in the invention without departing from the spirit and scope thereof.

What is claimed is:

1. An ultraviolet flaw detection light wherein the light is equipped with an ultraviolet light permeable filter comprising a dielectric multi-film layer which allows a visible radiation of a wave length range from 694 nm to 780 nm to reflect on the filter which prevents penetration of the wave length range from 694 nm to 780 nm through the filter and wherein the filter is on a surface of an ultraviolet light permeable filter glass.

2. An ultraviolet flaw detection light according to claim 1, wherein the dielectric multi-film layer is composed of alternating low refractivity membrane layers and high refractivity membrane layers.

3. An ultraviolet flaw detection light according to claim 1, wherein the dielectric multi-film layer is composed of plural layers while each single layer is constituted as a high refractivity membrane layer which is sandwiched by two low refractivity membrane layers.

* * * * *